(12) United States Patent
Wang (10) Patent No.: US 11,331,127 B2
(45) Date of Patent: May 17, 2022

(54) LOCKING STEEL PLATE AND LOCKING STEEL PLATE ASSEMBLY WITH LOCKING STEEL PLATE

(71) Applicant: Beijing AK Medical Co., Ltd., Beijing (CN)

(72) Inventor: Caimei Wang, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 0 days.

(21) Appl. No.: 16/960,921

(22) PCT Filed: Jan. 17, 2019

(86) PCT No.: PCT/CN2019/072101
§ 371 (c)(1),
(2) Date: Jul. 9, 2020

(87) PCT Pub. No.: WO2020/118852
PCT Pub. Date: Jun. 18, 2020

(65) Prior Publication Data
US 2021/0298805 A1    Sep. 30, 2021

(30) Foreign Application Priority Data

Dec. 11, 2018 (CN) .......................... 201811514078.X (51) Int. Cl.
*A61B 17/80* (2006.01)
*A61B 17/64* (2006.01)

(52) U.S. Cl.
CPC .......... *A61B 17/8052* (2013.01); *A61B 17/64* (2013.01); *A61B 17/8042* (2013.01)

(58) Field of Classification Search
CPC . A61B 17/80; A61B 17/8028; A61B 17/8033; A61B 17/8047; A61B 17/8052; A61B 17/82
See application file for complete search history.

(56) References Cited

U.S. PATENT DOCUMENTS 8,696,715 B2 * 4/2014 Sidebotham ....... A61B 17/8047
606/291
9,101,423 B2 * 8/2015 Hulliger ............. A61B 17/8057
(Continued)

FOREIGN PATENT DOCUMENTS

| CH | 701346 A2 | 12/2010 |
|---|---|---|
| CN | 2782036 Y | 5/2006 |

(Continued)

OTHER PUBLICATIONS

The extended European search report for the corresponding EP patent application No. 19861303 6, dated Dec. 8, 2020.

*Primary Examiner* — Larry E Waggle, Jr.
(74) *Attorney, Agent, or Firm* — Gang Yu (57) ABSTRACT

Provided are a locking steel plate and a locking steel plate assembly with the locking steel plate. Herein, the locking steel plate may include a steel plate body, an elastic block hook and a limit groove. The steel plate body is provided with a mounting hole, and the mounting hole may include a first hole section and a second hole section having a cross section area less than that of the first hole section. The elastic block hook is provided inside the first hole section, a first end of the elastic block hook is connected with the steel plate body, and a second end of the elastic block hook bends toward the second hole section. The limiting groove is provided on an inner wall of the second end of the elastic block hook.

17 Claims, 11 Drawing Sheets

(56) References Cited

U.S. PATENT DOCUMENTS

| | | | |
|---|---|---|---|
| 9,545,275 B2* | 1/2017 | Cawley | A61B 17/7059 |
| 2011/0184415 A1* | 7/2011 | Anderson | A61B 17/8047 |
| | | | 606/70 |
| 2011/0202092 A1* | 8/2011 | Frigg | A61B 17/8085 |
| | | | 606/289 |
| 2012/0143193 A1 | 6/2012 | Hulliger | |
| 2014/0249587 A1 | 9/2014 | Cawley et al. | |

FOREIGN PATENT DOCUMENTS

| | | | |
|---|---|---|---|
| CN | 1819799 A | 8/2006 |
| CN | 101022767 A | 8/2007 |
| CN | 105208953 A | 12/2015 |
| CN | 107928776 A | 4/2018 |
| CN | 209285685 U | 8/2019 |
| EP | 1741399 A2 | 1/2007 |
| EP | 2907461 A1 | 8/2015 |
| WO | 8803781 A1 | 6/1988 |
| WO | 2017100196 A1 | 6/2017 |

* cited by examiner

LOCKING STEEL PLATE AND LOCKING STEEL PLATE ASSEMBLY WITH LOCKING STEEL PLATE

TECHNICAL FIELD

The disclosure relates to a technical field of orthopedic medical instruments, and in particular to a locking steel plate and a locking steel plate assembly with the locking steel plate.

BACKGROUND

In the related art, treatment of fracture may be accompanied by serious injury or infection of a soft tissue, and an external fixator may be taken as a main fixation mode for the treatment of fracture. A majority of traditional external fixators are heavy with a complicated appearance, and need to be fixed for a long time during the treatment. It may bring great inconvenience to daily life of a patient, and even affect a functional exercise of an affected limb. A locking steel plate, when used as the external fixator, has achieved a satisfactory result during treatment of open fracture and infectious fracture.

The locking steel plate is a fracture fixing device having a threaded hole, and the steel plate may become a screw angle fixing device when a screw having a threaded head is screwed into the threaded hole. The locking steel plate may have a locking hole and an unlocking hole at same time, as to allow the different screws to be screwed in. The steel plate on which a fixing screw and a fixing bolt may be screwed in at any angle is the locking steel plate substantially. The steel plate is fixed to achieve connection depending on an interlocking structure of the steel plate completely rather than a friction of a bone. A certain gap may be remained between the steel, plate and a bone surface, thereby eliminating an adverse effect of contact of the steel plate with the bone in presence of a stress and greatly improving blood supply and growth and recovery of a periosteum. Compression of the steel plate to the bone is completed by taking a main biomechanical difference of a traditional steel plate as a friction force depending on a bone-steel plate interface.

When the abovementioned locking steel plate is implanted into the bone subjected to the fracture, the locked locking steel plate may get loose due to the blood supply and the growth and recovery of the periosteum, and an additional assembly may need to be added to prevent the locked locking steel plate from getting loose. However, the additional assembly may bring a certain risk to the blood supply and the growth and recovery of the periosteum. In addition, an operation may become inconvenient after adding the additional assembly.

SUMMARY

The disclosure is intended to provide a locking steel plate and a locking steel plate assembly with the locking steel plate, as to solve the problem in the related art that an operation may become inconvenient when an additional assembly prevents the locking steel plate from getting loose.

In order to achieve the abovementioned objective, in accordance with one aspect of the disclosure, a locking steel plate is provided, including a steel plate body, an elastic block hook and a limiting groove. The steel plate body is provided with a mounting hole, and the mounting hole may include a first hole section and a second hole section having a cross section area less than that of the first hole section. The elastic block hook is provided inside the first hole section, a first end of the elastic block hook is connected with the steel plate body, and a second end of the elastic block hook bends toward the second hole section. The limiting groove is provided on an inner wall of the second end of the elastic block hook.

In some embodiments, the mounting hole may further include a step surface connecting the first hole section and the second hole section, and the elastic block hook is provided on the step surface.

In some embodiments, an avoiding groove is formed between an outer wall of the elastic block hook and a hole wall of the first hole section.

In some embodiments, there are multiple elastic block hooks, the multiple elastic block hooks are uniformly provided along a circumferential direction of the mounting hole, and there is a gap between two adjacent elastic block hooks of the multiple of elastic block hooks.

In some embodiments, a size of an opening of the limiting groove is less than a maximum width of the limiting groove.

In some embodiments, an inner wall surface of the elastic block hook is an arc surface.

In some embodiments, an outer wall of the second end of the elastic block hook is provided with a guiding slope.

In some embodiments, the locking steel plate may further include multiple connecting hooks provided on one end of the steel plate body, the multiple connecting hooks are provided at intervals with identical orientation, and each of the multiple the connecting hooks bends toward a surface of the steel plate body.

In some embodiments, the steel plate body may include a basal plate layer and a micropore structure layer, a bottom of the basal plate layer, corresponding to the mounting hole, is provided with a thickened convex portion, the micropore structure layer is provided at an area of the basal plate layer other than the thickened convex portion, and a bottom surface of the thickened convex portion is aligned to a bottom surface of the micropore structure layer.

In accordance with another aspect of the disclosure, a locking steel plate assembly is provided, including a locking steel plate and a screw cooperating with the locking steel plate. The locking steel plate is the abovementioned locking steel plate. The screw may include a screw head and a screw rod, the screw head is accommodated in the elastic block hook of the locking steel plate, and the screw rod gets through the second hole section of the locking steel plate. The screw may further include a flange provided on the screw head, and the flange is provided at the limiting groove.

In accordance with another aspect of the disclosure, a locking steel plate assembly is provided, including multiple locking steel plates connected with each other. Each of the multiple locking steel plates is the abovementioned locking steel plate. A groove is formed by two adjacent locking steel plates in multiple locking steel plates at a butt-joint position, the connecting hook of the each of multiple locking steel plates is positioned in the groove, and orientations of the connecting hooks of two adjacent locking steel plates in the multiple locking steel plates are opposite to each other.

With the adoption of the technical solution of the disclosure, the locking steel plate is provided with the elastic block hook and the limiting groove additionally. The steel plate body is provided with the mounting hole, and the mounting hole may include the first hole section and the second hole section having the cross section area less than that of the first hole section. The elastic block hook is provided inside the first hole section, the first end of the elastic block hook is connected with the steel plate body, and the second end of the elastic block hook bends toward the second hole section. The limiting groove is provided on the inner wall of the second end of the elastic block hook. In the disclosure, under a situation that the steel plate body cooperates with the screw, the screw is mounted in the mounting hole and implanted into a bone. The elastic block hook provided inside the first hole section may lock the screw inside the steel plate body, thereby preventing the screw from dropping out and playing a role of blocking. The limiting groove cooperates with the screw head of the screw, thereby further preventing the screw from dropping out. In the disclosure, the locking steel plate has no additional assembly, and inconvenient operation caused by the additional assembly does not need to be considered. In addition, the elastic block hook occupies a small space, and a structural strength of the steel plate body may not be weakened.

BRIEF DESCRIPTION OF THE DRAWINGS

The accompanying drawings described herein are used to provide a further understanding of the disclosure, and constitute a part of the present application, and the exemplary embodiments of the disclosure and the description thereof are used to explain the disclosure, but do not constitute improper limitations to the disclosure. In the drawings.

Herein, the abovementioned drawings may include reference numbers below:

1. Locking steel plate; 2. Screw; 2*a*. Screw head; 2*b*. Screw rod; 2*c*. Flange; 3. Bone; 4. Steel wire; 5. Fracture line; 6. Groove; 10. Steel plate body; 11. Mounting hole; 111. First hole section; 112. Second hole section; 113. Step surface; 114. Avoiding groove; 12. Connecting hook; 13. Basal plate layer; 131. Thickened convex portion; 14. Micropore structure layer; 20. Elastic block hook; 21. Guiding slope; 30. Limiting groove.

DETAILED DESCRIPTION OF THE EMBODIMENTS

The technical solutions in the embodiments of the disclosure will be clearly and completely described below in combination with the drawings in the embodiments of the disclosure. It is apparent that the described embodiments are not all embodiments but part of embodiments of the disclosure. The description of at least one exemplary embodiment below is illustrative only in fact, and is never intended to limit the disclosure and its application or use. All other embodiments obtained by those of ordinary skilled in the art on the basis of the embodiments in the disclosure without creative work shall fall within the scope of protection of the disclosure.

It is to be noted that terms used here are to describe a specific embodiment only and not intended to limit the exemplary embodiment in accordance with the application. If it is used here, unless otherwise clearly specified in the context, a singular form should be intended to include a plural form. In addition, it is to be understood that when the term "include" and/or "comprise" is used in the description, it indicates that there is a feature, a step, an operation, a device, a component and/or their combinations.

Unless otherwise specifically stated, a relative arrangement of the part and the step, a number expression and a value clarified in these embodiments may not limit the scope of the disclosure. Meanwhile, it is to be understood that, in order to facilitate description, a size of each part shown in the figure is not drawn in accordance with an actual proportional relation. A technology, a method and a device known by those of ordinary skilled in the related art may not be discussed in detail. However, the technology, the method and the device should be deemed as one part of an authorization description under appropriate conditions. In all examples shown and discussed here, any specific values should be explained to be exemplary merely rather than be restrictive. Therefore, other examples of the exemplary embodiments may have different values. It is to be noted that a similar reference number and a similar letter may represent similar terms in the figure below. Therefore, once defined in one figure, an item does not need to be further discussed in a subsequent figure.

Figure 1:
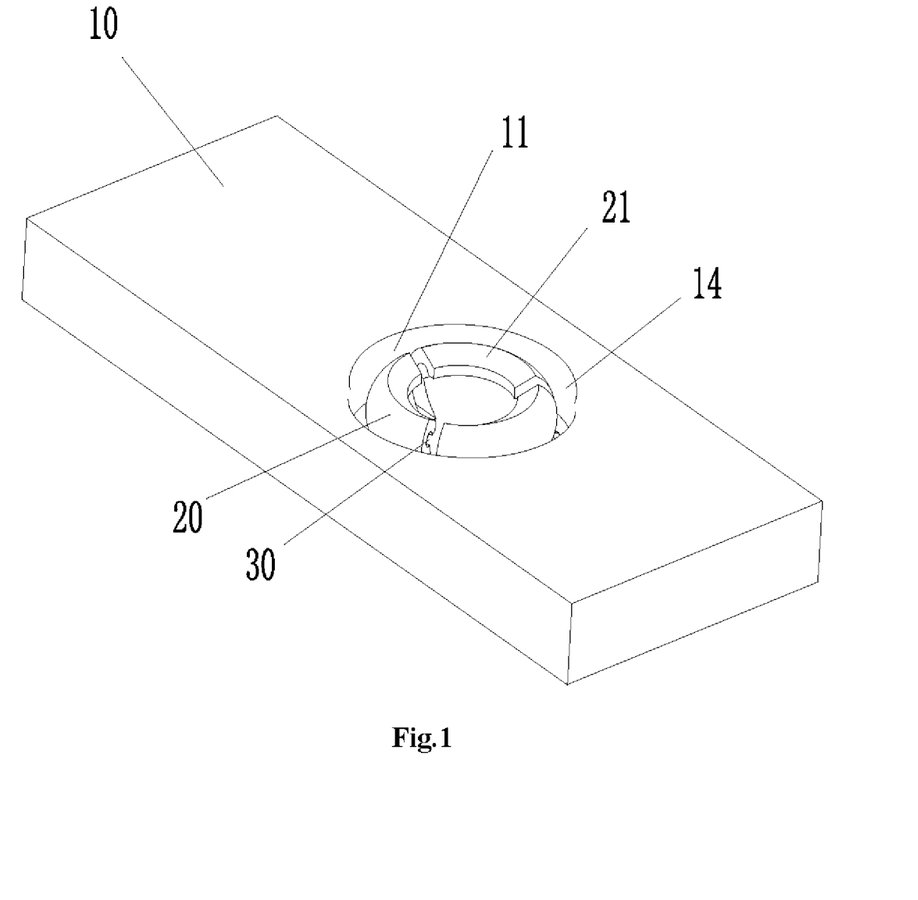
FIG. 1 shows a stereo structure diagram of an embodiment 1 of a locking steel plate in accordance with the disclosure.
Figure 3:
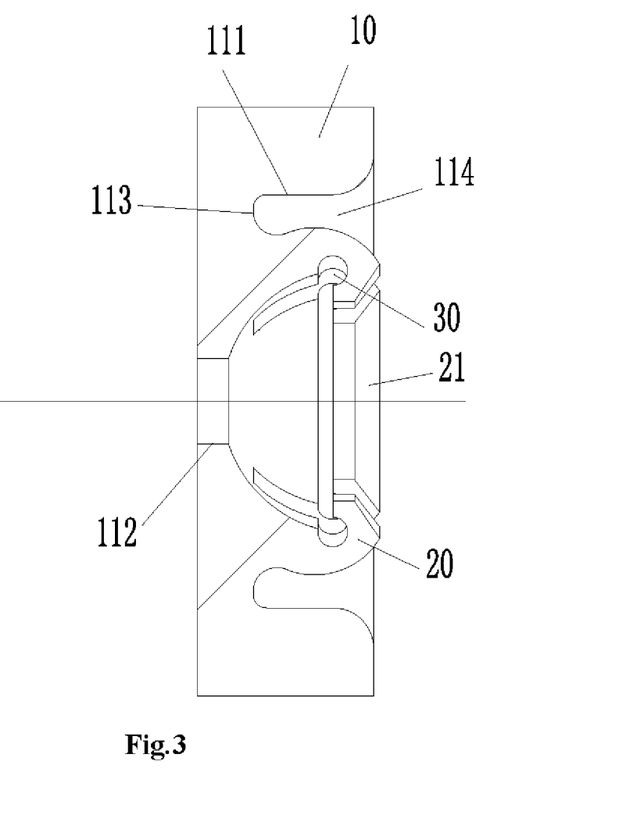
FIG. 3 shows an A-A direction section view of a locking steel plate in FIG. 2.

As shown in FIG. 1 and FIG. 3, a locking steel plate of an embodiment 1 may include a steel plate body 10, an elastic block hook 20 and a limiting groove 30. The steel plate body 10 is provided with a mounting hole 11, and the mounting hole 11 may include a first hole section 111 and a second hole section 112 having a cross section area less than that of the first hole section 111. The elastic block hook 20 is provided inside the first hole section 111, a first end of the elastic block hook 20 is connected with the steel plate body 10, and a second end of the elastic block hook 20 bends toward the second hole section 112. The limiting groove 30 is provided on an inner wall of the second end of the elastic block hook 20.

With the adoption of the technical solution of the embodiment 1, the locking steel plate is provided with the elastic block hook and the limiting groove additionally. The steel plate body 10 is provided with the mounting hole 11, and the mounting hole 11 may include the first hole section 111 and the second hole section 112 having the cross section area less than that of the first hole section 111. The elastic block hook 20 is provided inside the first hole section 111, the first end of the elastic block hook 20 is connected with the steel plate body 10, and the second end of the elastic block hook 20 bends toward the second hole section 112. The limiting groove 30 is provided on the inner wall of the second end of the elastic block hook 20. In the embodiment 1, under a situation that the steel plate body 10 cooperates with a screw, the screw is mounted inside the mounting hole 11 and implanted onto a bone. The elastic block hook 20 provided inside the first hole section 111 may lock the screw inside the steel plate body 10, thereby preventing the screw from dropping out and playing a role of blocking. The limiting groove 30 cooperates with a screw head of the screw, thereby further preventing the screw from dropping out. In addition, the locking steel plate has no additional assembly, and inconvenient operation caused by the additional assembly does not need to be considered. In addition, the elastic block hook 20 occupies a small space, and a structural strength of the steel plate body 10 may not be weakened.

Figure 4:
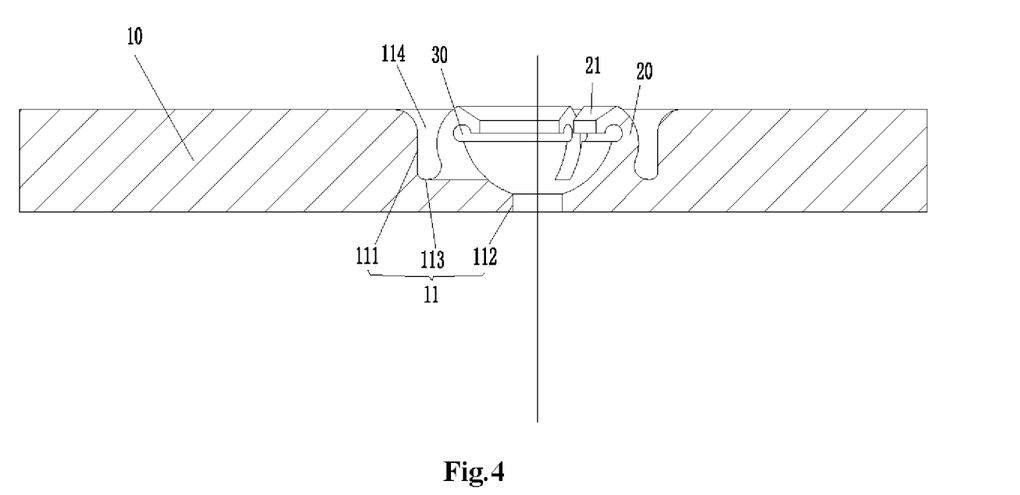
FIG. 4 shows a B-B direction section view of a locking steel plate in FIG. 2.

As shown in FIG. 3-4, the mounting hole 11 may further include a step surface 113 connecting the first hole section 111 and the second hole section 112, and the elastic block hook 20 is provided on the step surface 113. Due to the abovementioned configuration position, the elastic block hook 20 may be deformed easily, in this way the screw penetrates easily. In the embodiment 1, the elastic block hook 20 does not protrude out of the steel plate body 10, thereby making the elastic block hook 20 not be touched easily. Of course, when the elastic block hook 20 cooperates with the screw, the first hole section 111 and the second hole section 112 are configured to make the elastic block hook 20 not be touched easily as well, and accordingly ensure a locking effect of the screw.

As shown in FIGS. 3-4, in the embodiment 1, under a situation that the elastic block hook 20 is deformed, a certain deformation space needs to be provided preferably outside a circumferential direction of the elastic block hook 20 in order to prevent the elastic block hook 20 from interfering with a hole wall of the first hole section 111. An avoiding groove 114 is formed between an outer wall of the elastic block hook 20 and the hole wall of the first hole section 111. The avoiding groove 114 forms the abovementioned deformation space.

Figure 2:
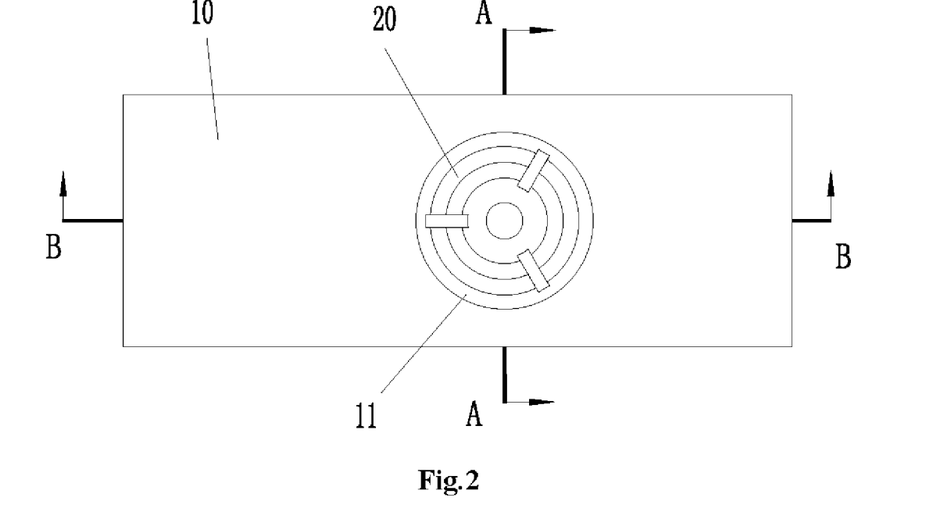
FIG. 2 shows a top view of a locking steel plate in FIG. 1.

As shown in FIGS. 1-2, in the embodiment 1, there are three elastic block hooks 20, the three elastic block hooks 20 are uniformly provided along a circumferential direction of the mounting hole 11, and there is a gap between two adjacent elastic block hooks 20. In this way, when the screw is screwed into the mounting hole 11, each of the elastic block hooks 20 may extend outward, and two adjacent elastic block hooks 20 may not extrude each other. The elastic block hook 20 is appropriately deformed, in order to facilitate screwing in the screw. In the other embodiments not shown in figures, a quantity of the elastic block hooks is not limited to 3, and may be 2, 4 and above.

As shown in FIGS. 3-4, in the embodiment 1, a size of an opening of the limiting groove 30 is less than a maximum width of the limiting groove 30. In this way, when the screw is screwed in within the elastic block hooks 20, an external edge of the screw may be blocked inside the limiting groove 30 tightly, without dropping out from the opening of the limiting groove 30 easily. Accordingly, the screw is prevented from dropping out. In the embodiment 1, a cross section of the limiting groove 30 is an arc, and the size of the opening of the limiting groove 30 is less than a diameter of the limiting groove 30.

As shown in FIGS. 3-4, in the embodiment 1, in order to make the screw tightly fit the elastic block hook 20 and to accordingly improve locking stability, an inner wall surface of the elastic block hook 20 is an arc surface. Correspondingly, an arc is provided at a position where the screw cooperates with the arc surface.

As shown in FIG. 1 and FIG. 3, in the embodiment 1, in order to smoothly screw the screw into the elastic block hook 20, an outer wall of the second end of the elastic block hook 20 is provided with a guiding slope 21.

Figure 12:
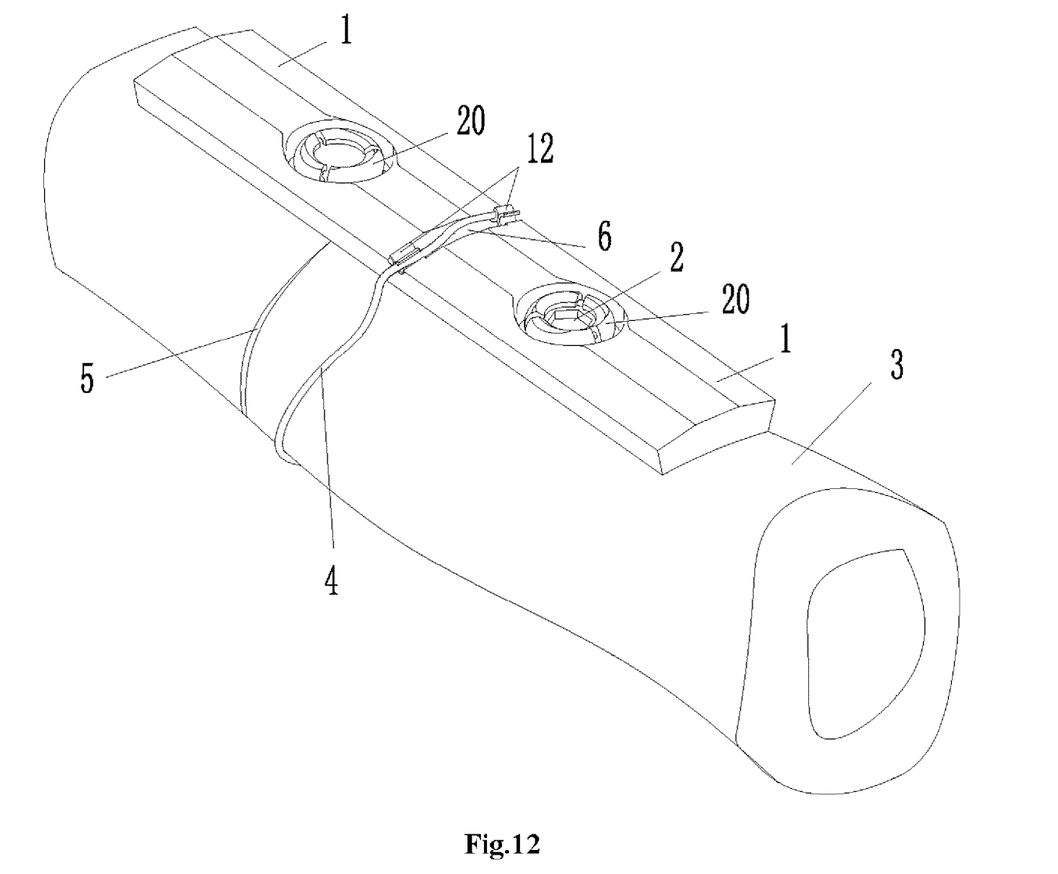
FIG. 12 shows a structure diagram of two locking steel plate assemblies in FIG. 5 connected with a bone.

As shown in FIG. 12, the locking steel plate may further include two connecting hooks 12 provided on one end of the steel plate body 10, the two connecting hooks 12 are provided at intervals with identical orientation, and the connecting hook 12 bends toward a surface of the steel plate body 10.

In the related art, as for use of a steel wire, there are two modes available generally on the steel plate: mode 1, the locking steel plate is provided with a groove, and the groove in the structure may easily lead to disengagement and slipping of the steel wire; and mode 2, the locking steel plate is provided with a long hole. A long-hole structure avoids a defect of a groove structure, however the steel wire needs to go through the hole, and it is difficult to operate during an operation.

The structure of the embodiment 1 may excellently solve the problems of the abovementioned two modes, no disengagement and slipping may occur when the connecting hook 12 cooperates with the steel wire 4, and operation of making the steel wire get through the hole may not be required when the connecting hook 12 cooperates with the steel wire 4. Therefore, disengagement may not occur and no steel wire is required to get through the hole when two connecting hooks on the steel plate body 10 cooperate with the steel wire 4, and the function of binding or restraining the steel plate body 10 can be achieved as well. In the other embodiments not shown in figures, a quantity of the connecting hooks provided on the steel plate body is not limited to 2, and may be 3 and above.

Figure 5:
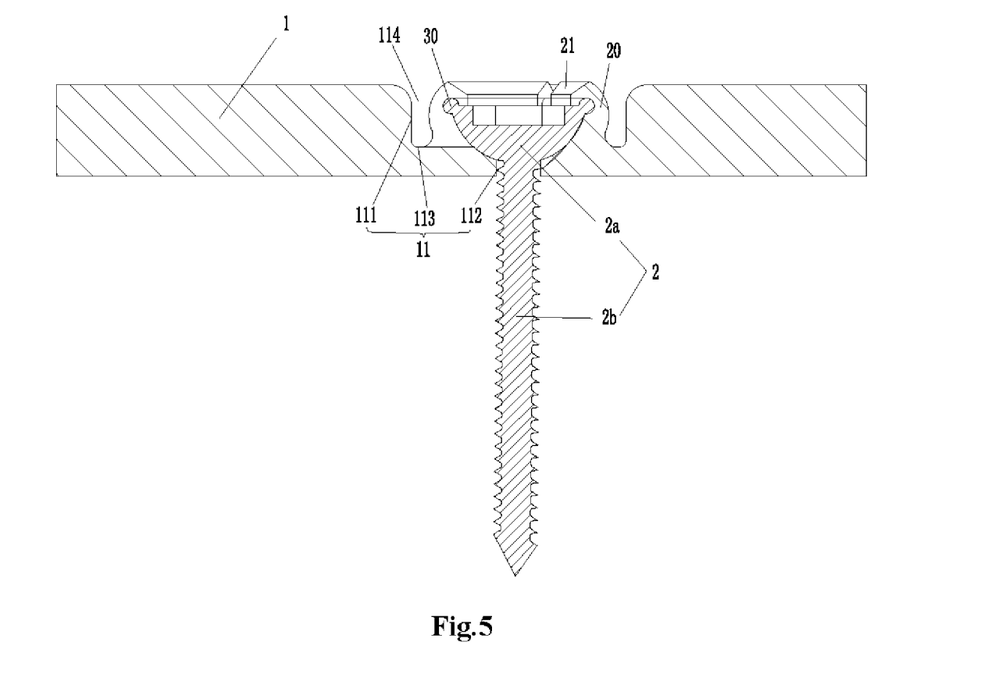
FIG. 5 shows a section view of an embodiment 1 of a locking steel plate assembly in accordance with the disclosure.
Figure 6:
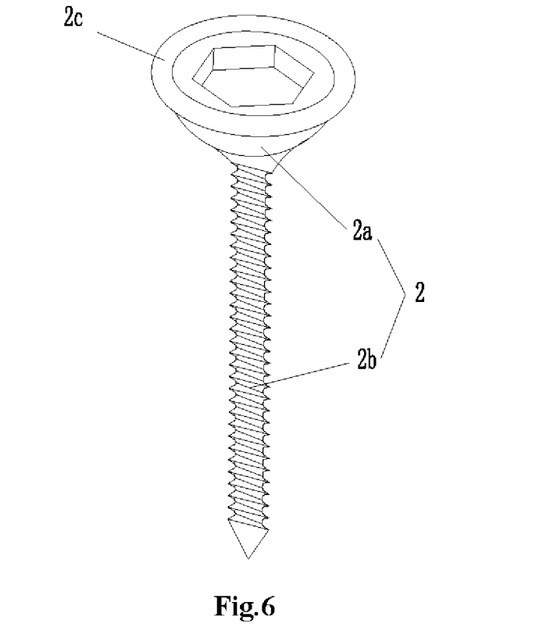
FIG. 6 shows a stereo diagram of a screw of a locking steel plate assembly in FIG. 5.
Figure 7:
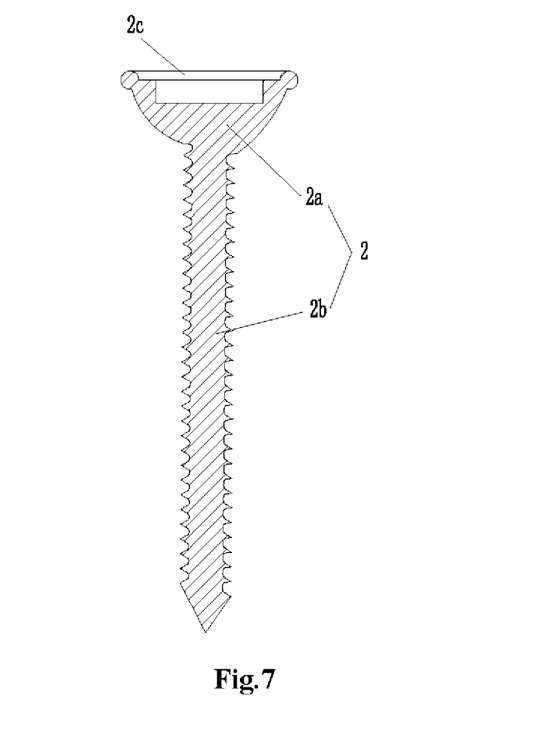
FIG. 7 shows a section view of a screw of a locking steel plate assembly in FIG. 6.

The disclosure further provides a locking steel plate assembly. As shown in FIGS. 5-7, the locking steel plate in the embodiment 1 may include a locking steel plate 1 and a screw 2 cooperating with the locking steel plate 1, the locking steel plate is the abovementioned locking steel plate, and the abovementioned locking steel plate may solve the inconvenient operation caused when an additional assembly prevents the locking steel plate from getting loose in the related art. The screw 2 may include a screw head 2a and a screw rod 2b, the screw head 2a is accommodated in an elastic block hook 20 of the locking steel plate 1, and the screw rod 2b goes through a second hole section 112 of the locking steel plate 1. The screw 2 may further include a flange 2c provided on the screw head 2a, and the flange 2c is provided at a limiting groove 30. The flange 2c in the embodiment 1 cooperates with the limiting groove 30, thereby making the flange 2c limited in the limiting groove 30 firmly and ensuring that the limiting groove 30 plays a role of preventing the screw 2 from dropping out. In the embodiment, a cross section of the flange 2c is an arc, and a diameter of its cross section is about 1 mm preferably.

As shown in FIGS. 5-7, the limiting groove 30 of the locking steel plate 1 is an arc groove, the flange 2c is annular, and an outer surface of the flange 2c is shown as an arc. In this way, the limiting groove 30 and the flange 2c are facilitated to achieve cooperation. In addition, before mounting the screw 2, the flange 2c is annular and may not hurt a user easily.

Figure 8:
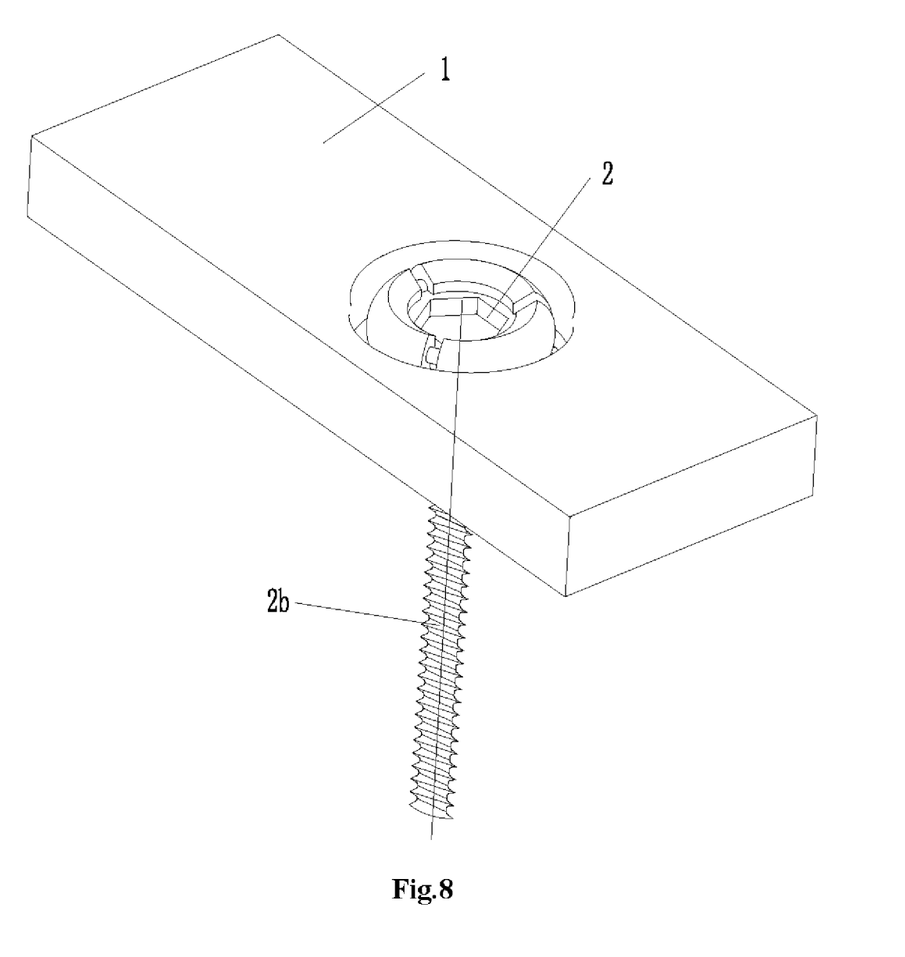
FIG. 8 shows a stereo diagram of an embodiment 2 of a locking steel plate assembly of the disclosure.
Figure 9:
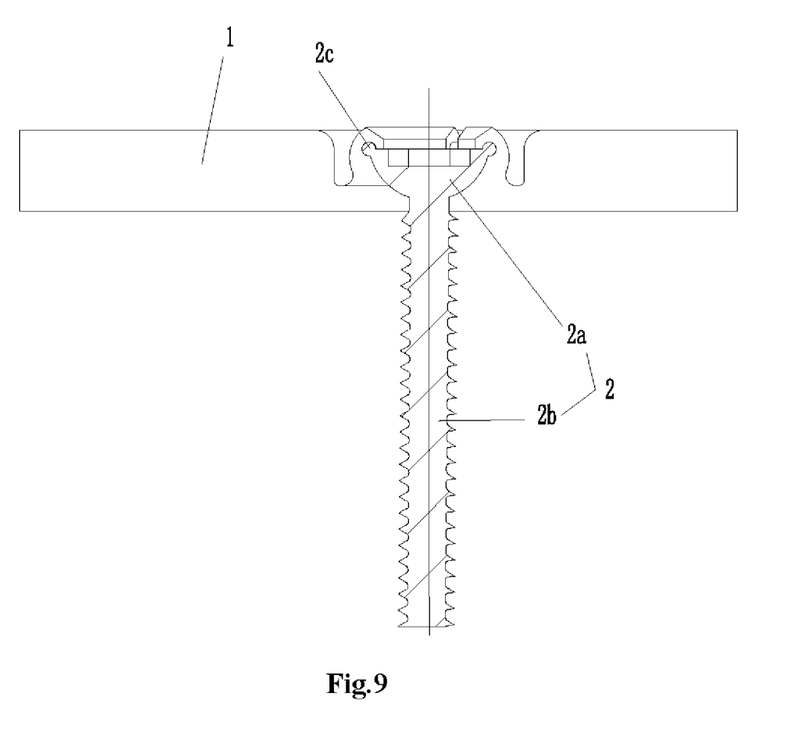
FIG. 9 shows a section view of a locking steel plate assembly in FIG. 8.

As shown in FIGS. 8-9, in an embodiment 2 of the locking steel plate assembly of the disclosure, distinguished from the embodiment 1, the screw rod 2b does not have a tip thereon. In the embodiment 2, the screw 2 is screwed into the locking steel plate 1 and the flange 2c of the screw 2 is limited in the limiting groove. In this way, the limiting groove may play a role of preventing the screw from dropping out.

Figure 10:
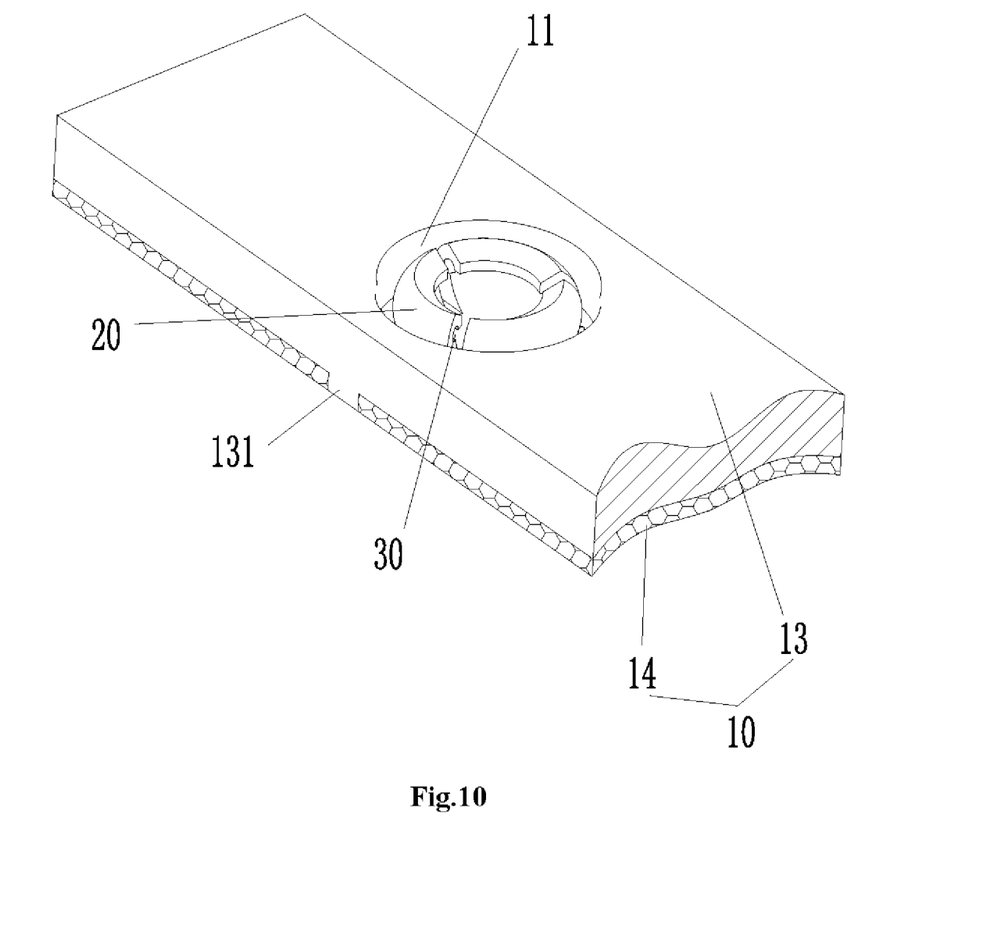
FIG. 10 shows a stereo structure diagram of an embodiment 2 of a locking steel plate of the disclosure.
Figure 11:
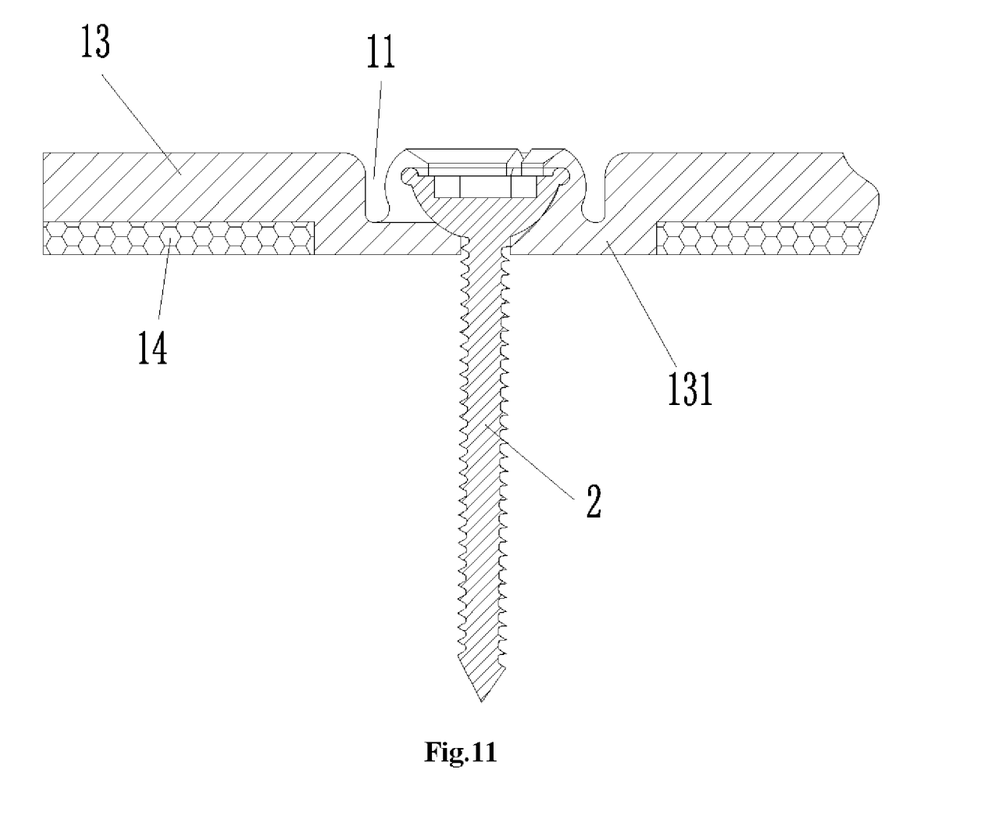
FIG. 11 shows a section view when a locking steel plate in FIG. 10 cooperates with a screw.

As shown in FIGS. 10-11, in the embodiment 2 of the locking steel plate of the disclosure, distinguished from the embodiment 1, there is a specific structure of a steel plate body of the embodiment 2. In the embodiment 2, the steel plate body 10 may include a basal plate layer 13 and a micropore structure layer 14, a bottom of the basal plate layer 13, corresponding to a mounting hole 11, is provided with a thickened convex portion 131, the micropore structure layer 14 is provided at an area of the basal plate layer 13 other than the thickened convex portion 131, and a bottom surface of the thickened convex portion 131 is aligned to a bottom surface of the micropore structure layer 14. The thickened convex portion 131 may ensure a connecting strength of the mounting hole 11. The micropore structure layer 14 has good bone fusion which may facilitate a bone to grow inward and has good integrating capability with the bone 3.

Figure 13:
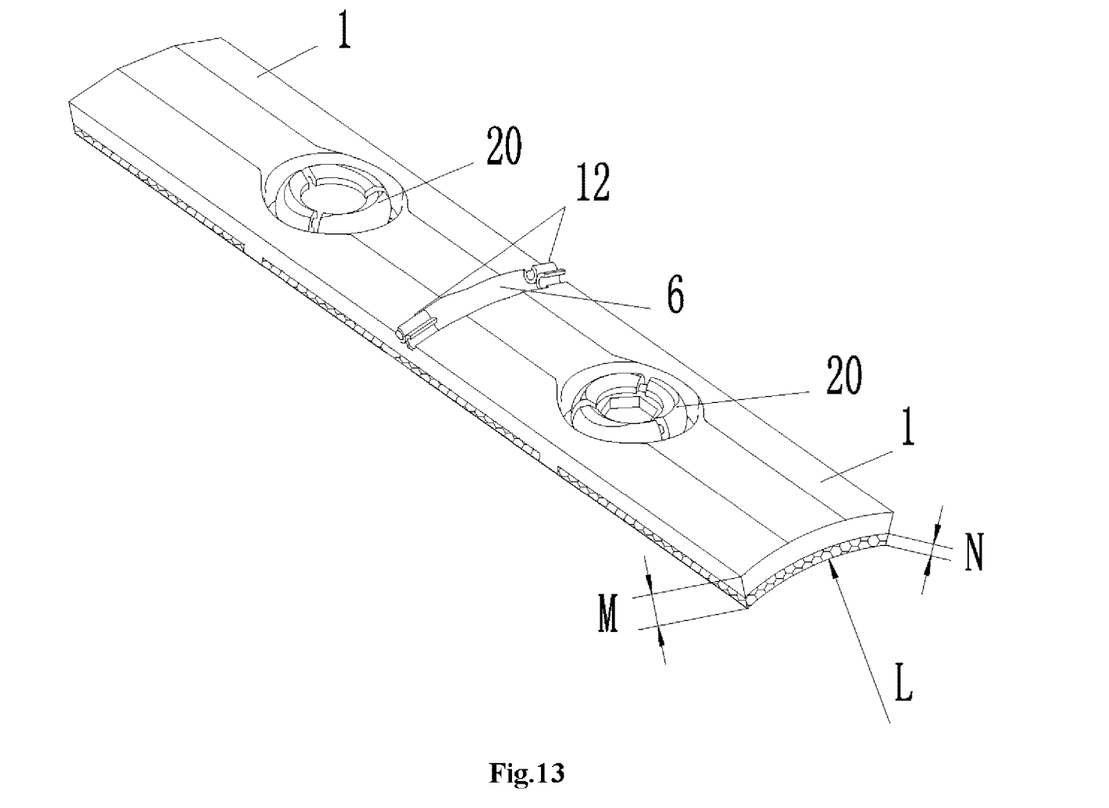
FIG. 13 shows a stereo diagram of two locking steel plates cooperating with each other in FIG. 10.
Figure 14:
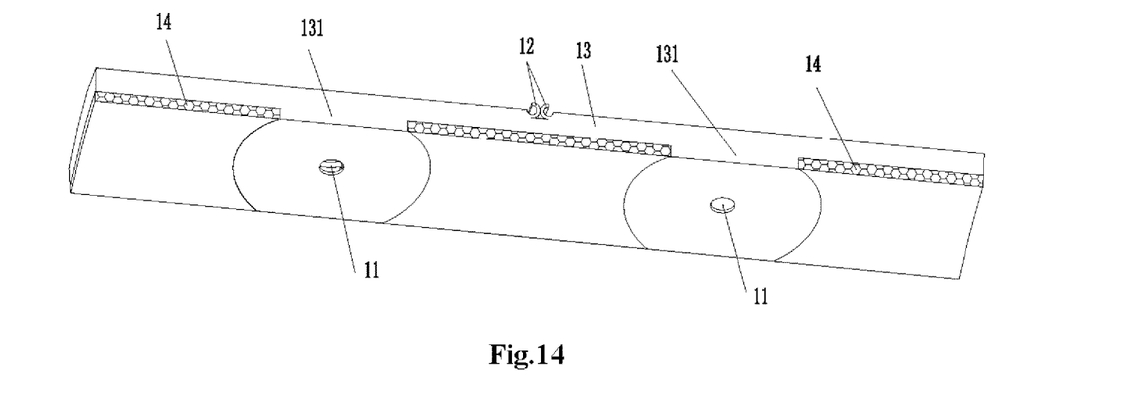
FIG. 14 shows a stereo structure diagram of another direction of two locking steel plates in FIG. 13.

In the embodiment 2, as shown in FIG. 13, a thickness M of the steel plate body 10 is 2.5-7 mm, and a thickness N of the micropore structure layer 14 is 1-3 mm. The bottom surface of the micropore structure layer 14 contacting with the bone 3 is an arc surface, and a radius L of a circle where the arc surface is 15-30 mm. The abovementioned structural size may be compatible with the bone fusion of the micropore structure layer 14 and an overall connecting strength of the steel plate body 10. In this way, the steel plate body 10 may have an optimal working performance.

The basal plate layer 13 and the micropore structure layer 14 may be acquired through 3D printing. Multiple pores are formed on the abovementioned micropore structure layer 14, like bone trabecula structures in the related art. A bone trabecula in the related art is an extension part of a bone cortex inside a cancellous bone, namely, the bone trabecula is connected with the bone cortex. An irregular stereo reticular formation is shown in a bone network cavity, thereby playing a role of supporting a hematopoietic tissue like a loofah or sponge.

Figure 15:
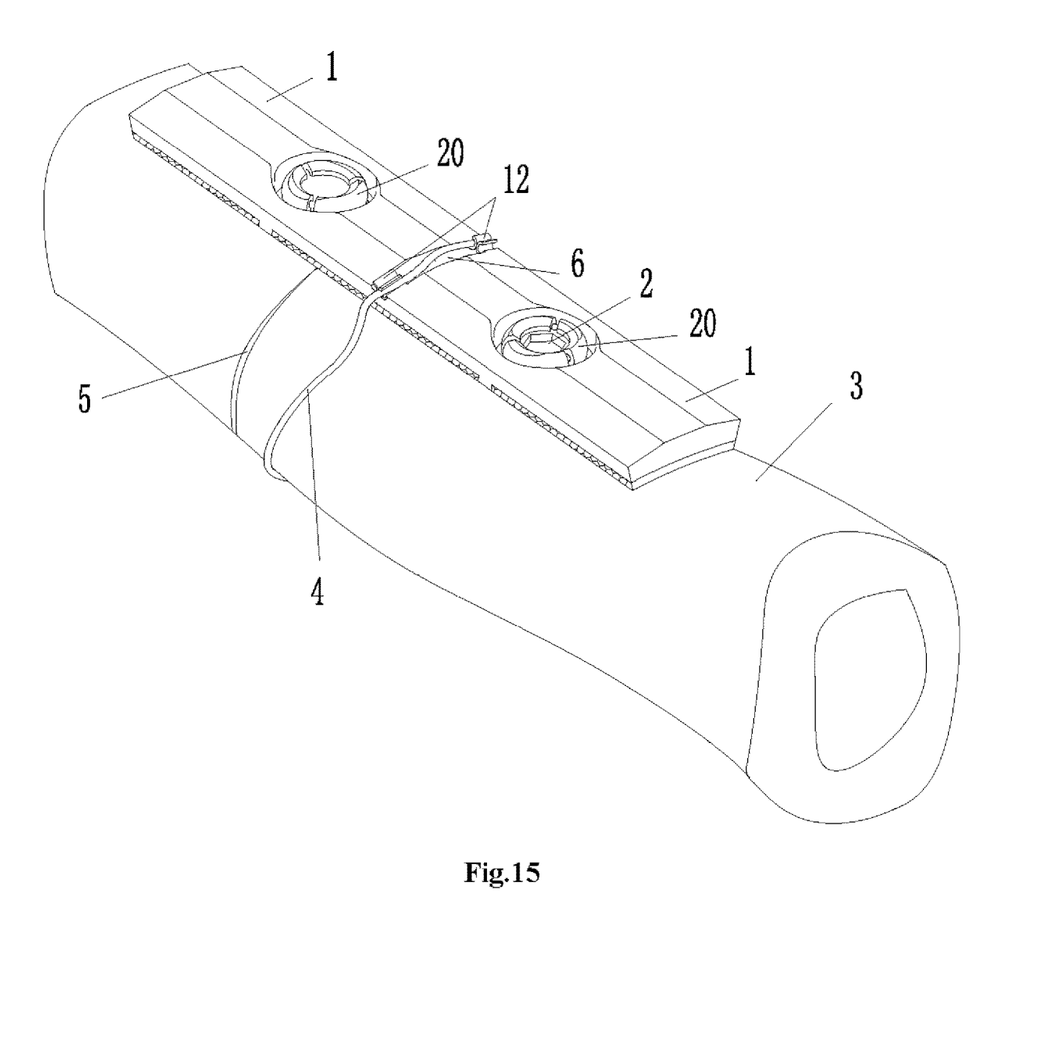
FIG. 15 shows a structure diagram of two locking steel plates and a screw in FIG. 10 connected with a bone.

The disclosure further provides a locking steel plate assembly. As shown in FIG. 12 and FIG. 15, an embodiment of the locking steel plate assembly in accordance with the disclosure may include multiple locking steel plates 1 connected with each other. Each of the locking steel plates is the abovementioned locking steel plate, and the abovementioned locking steel plate may solve the inconvenient operation caused when an additional assembly prevents the locking steel plate from getting loose in the related art. A groove 6 is formed by two adjacent locking steel plates 1 at a butt-joint position, a connecting hook 12 of each of the locking steel plates 1 is positioned in the groove 6, and orientations of the connecting hooks 12 of two adjacent locking steel plates 1 are opposite to each other.

A steel plate body of the locking steel plate assembly shown in FIG. 12 does not include a micropore structure layer, and the steel plate body of the locking steel plate assembly shown in FIG. 15 may include a micropore structure layer. A remaindering part of the locking steel plate assembly in FIG. 12 is the same as that in FIG. 15. As shown in FIGS. 12-15, multiple locking steel plates 1 are connected together, thereby forming a whole locking steel plate assembly, and the groove 6 is formed by two adjacent locking steel plates 1 at the butt-joint position. The whole locking steel plate assembly may include multiple mounting holes 11 and at least one groove 6. The mounting hole 11 allows a screw 2 to get through, and the groove 6 is configured to make a steel wire 4 get through. Two ends of the groove 6 are provided with two groups of connecting hooks 12 having opposite directions, and the steel wire 4 may selectively catch the connecting hooks 12 of different directions. When selecting the connecting hooks 12 of the different directions, the steel wire 4 may be fixed easily, thereby preventing the steel wire 4 from getting loose toward one direction. In the embodiment, the whole locking steel plate assembly may include two mounting holes 11 and one groove 6. FIG. 12 and FIG. 15 show a fracture line 5, respectively.

Specifically, when fixing the locking steel plate 1, the screw 2 is screwed into a bone 3, mainly for fixation. At the moment, the steel wire 4 may be selected to fix. When bundling with the steel wire 4, as shown in FIG. 12 and FIG. 15, a right end of a left locking steel plate 1 is provided with two connecting hooks 12, and a left end of a right locking steel plate 1 is provided with two connecting hooks 12 as well. When the left locking steel plate 1 and the right locking steel plate 1 are docked, orientations of the connecting hooks 12 at corresponding positions may be opposite. The steel wire 4 may achieve fixation after going around an upper connecting hook 12 on the left locking steel plate 1, going across the right locking steel plate 1, and going around a lower connecting hook 12 on the right locking steel plate 1 and subsequently going around the bone 3. With the adoption of a fixation mode, the steel wire 4 may be prevented from getting loose and slipping because a screwing force is insufficient during long-term creep, compared with a situation in which there is no connecting hook available or the connecting hooks on the two sides are in the same direction.

In the descriptions of the disclosure, it is to be understood that orientation or position relationships indicated by nouns of locality, such as "front", "back", "upper", "lower", "left", "right", "transverse", "longitudinal", "vertical", "horizontal", "top", "bottom" are generally orientation or position relationships shown in the drawings, are adopted not to indicate or imply that indicated devices or components must be in specific orientations or structured and operated in specific orientations but only to conveniently describe the disclosure and simplify descriptions and thus should not be understood as limits to the disclosure when there is no contrary statement available. The nouns of locality "inside", "outside" are the inside and outside relative to an outline of each part.

In order to facilitate description, a spatial relative term may be used here, such as "over", "above", "on an upper surface" and "on", to describe a spatial position relation between a device or a feature shown in the figure and other devices or other features. It is to be understood that the spatial relative term is intended to include different orientations of the device during use or operation outside the orientation described in the figure. For example, if the device in the figure is inverted, it may be described as that the device "above other devices or other structures" or "over other devices or other structures" shall be positioned "below other devices or other structures" or "under other devices or other structures". Therefore, an exemplary term "above" may include two orientations: "above" and "below". As an alternative, the device may be positioned with other different modes (90° rotation or positioned at other orientations), and the spatial relative description used here needs to be explained correspondingly.

In addition, it is to be noted that the terms "first", "second" and the like are adopted to limit the parts and to facilitate distinguishing corresponding parts only. Unless otherwise stated, the abovementioned terms do not have any special meaning and accordingly should not be understood as the limits to the scope of protection of the disclosure.

The above is only the preferred embodiment of the disclosure and not intended to limit the disclosure. For those skilled in the art, the disclosure may have various modifications and variations. Any modifications, equivalent replacements, improvements and the like made within the spirit and principle of the disclosure shall fall within the scope of protection of the disclosure.

What is claimed is:

1. A locking steel plate, comprising:
   a steel plate body, the steel plate body being provided with a mounting hole, and the mounting hole comprising a first hole section and a second hole section having a cross section area less than a cross section area of the first hole section;
   an elastic block hook, provided inside the first hole section, a first end of the elastic block hook being connected with the steel plate body, and a second end of the elastic block hook bending toward the second hole section; and
   a limiting groove, provided on an inner wall of the second end of the elastic block hook;
   a size of an opening of the limiting groove is less than a maximum width of the limiting groove.

2. The locking steel plate as claimed in claim 1, wherein, the mounting hole further comprises a step surface connecting the first hole section and the second hole section, and the elastic block hook is provided on the step surface.

3. The locking steel plate as claimed in claim 2, wherein, an avoiding groove is formed between an outer wall of the elastic block hook and a hole wall of the first hole section.

4. The locking steel plate as claimed in claim 1, wherein, there are a plurality of elastic block hooks, the plurality of elastic block hooks are uniformly provided along a circumferential direction of the mounting hole, and there is a gap between two adjacent elastic block hooks of the plurality of elastic block hooks.

5. The locking steel plate as claimed in claim 1, wherein, an inner wall surface of the elastic block hook is an arc surface.

6. The locking steel plate as claimed in claim 1, wherein, an outer wall of the second end of the elastic block hook is provided with a guiding slope.

7. The locking steel plate as claimed in claim 1, further comprising a plurality of connecting hooks provided on one end of the steel plate body, the plurality of connecting hooks being provided at intervals with identical orientation, and each of the plurality of connecting hooks bending toward a surface of the steel plate body.

8. A locking steel plate assembly, comprising a plurality of locking steel plates connected with each other, wherein, each of the plurality of locking steel plates is the locking steel plate as claimed in claim 7, a groove is formed by two adjacent locking steel plates in the plurality of locking steel plates at a butt-joint position, the connecting hook of the each of the plurality of locking steel plates is positioned in the groove, and orientations of the connecting hooks of two adjacent locking steel plates in the plurality of locking steel plates are opposite to each other.

9. The locking steel plate as claimed in claim 1, wherein, the steel plate body comprises a basal plate layer and a micropore structure layer, a bottom of the basal plate layer, corresponding to the mounting hole, is provided with a thickened convex portion, the micropore structure layer is provided at an area of the basal plate layer other than the thickened convex portion, and a bottom surface of the thickened convex portion is aligned to a bottom surface of the micropore structure layer.

10. A locking steel plate assembly, comprising the locking steel plate as claimed in claim 1 and a screw cooperating with the locking steel plate, wherein, the screw comprises a screw head and a screw rod, the screw head is accommodated in the elastic block hook of the locking steel plate, the screw rod gets through the second hole section of the locking steel plate, the screw further comprises a flange provided on the screw head, and the flange is provided in the limiting groove.

11. The locking steel plate assembly as claimed in claim 10, wherein, the mounting hole further comprises a step surface connecting the first hole section and the second hole section, and the elastic block hook is provided on the step surface.

12. The locking steel plate assembly as claimed in claim 11, wherein, an avoiding groove is formed between an outer wall of the elastic block hook and a hole wall of the first hole section.

13. The locking steel plate assembly as claimed in claim 10, wherein, there are a plurality of elastic block hooks, the plurality of elastic block hooks are uniformly provided along a circumferential direction of the mounting hole, and there is a gap between two adjacent elastic block hooks of the plurality of elastic block hooks.

14. The locking steel plate assembly as claimed in claim 10, wherein, an inner wall surface of the elastic block hook is an arc surface.

15. The locking steel plate assembly as claimed in claim 10, wherein, an outer wall of the second end of the elastic block hook is provided with a guiding slope.

16. The locking steel plate assembly as claimed in claim 10, wherein, the steel plate body comprises a basal plate layer and a micropore structure layer, a bottom of the basal plate layer, corresponding to the mounting hole, is provided with a thickened convex portion, the micropore structure layer is provided at an area of the basal plate layer other than the thickened convex portion, and a bottom surface of the thickened convex portion is aligned to a bottom surface of the micropore structure layer.

17. A locking steel plate, comprising:
    a steel plate body, the steel plate body being provided with a mounting hole, and the mounting hole comprising a first hole section and a second hole section having a cross section area less than a cross section area of the first hole section;
    an elastic block hook, provided inside the first hole section, a first end of the elastic block hook being connected with the steel plate body, and a second end of the elastic block hook bending toward the second hole section; and
    a limiting groove, provided on an inner wall of the second end of the elastic block hook;
    the locking steel plate further comprising a plurality of connecting hooks provided on one end of the steel plate body, the plurality of connecting hooks being provided at intervals with identical orientation, and each of the plurality of connecting hooks bending toward a surface of the steel plate body.

* * * * *